US00PP23040P3

(12) United States Plant Patent
Shurtleff

(10) Patent No.: US PP23,040 P3
(45) Date of Patent: Sep. 18, 2012

(54) ***OLEA EUROPAEA* TREE NAMED 'HIDSHURTLEFF'**

(50) Latin Name: *Olea europaea*
Varietal Denomination: HIDshurtleff

(76) Inventor: Blair Shurtleff, San Luis Obispo, CA (US)

( * ) Notice: Subject to any disclaimer, the term of this patent is extended or adjusted under 35 U.S.C. 154(b) by 5 days.

(21) Appl. No.: 12/925,836

(22) Filed: Oct. 29, 2010

(65) Prior Publication Data

US 2012/0110708 P1 May 3, 2012

(51) Int. Cl.
*A01H 5/00* (2006.01)

(52) U.S. Cl. ..... Plt./158

(58) Field of Classification Search ..... Plt./158
See application file for complete search history.

*Primary Examiner* — Susan McCormick Ewoldt
(74) *Attorney, Agent, or Firm* — Kauth, Pomeroy, Peck & Bailey LLP

(57) ABSTRACT

A variety of olive tree, named 'HIDshurtleff'. The 'HIDshurtleff' is an ornamental olive tree having a bright green leaf with a smooth texture and increased width and length, a very long weeping characteristic, extremely low leaf/material drop, and very hardy wind, animal and drought characteristics.

2 Drawing Sheets

Classification: The present invention relates to a new *Olea Europaea* tree.

Variety denomination: The new plant has the varietal denomination 'HIDshurtleff'.

ORIGIN OF INVENTION

This invention relates to a new and distinct variety of *Olea europaea* named 'HIDshurtleff', which was discovered in a garden in Santa Margarita, Calif. The plant to date is known only to exist within the boundaries of the garden in which it was found, and has not been offered for sale or described in any publication. The parentage of the plant is 'unknown'. The mutation of the tree occurred across the whole plant.

SUMMARY OF THE INVENTION

Among the features which distinguish the new variety from other presently available and commercial olive cultivars known to the inventor is the following combination of characteristics: a bright green leaf having a smooth texture and increased width and length, a very long weeping characteristic, extremely low leaf/material drop, and very hardy wind, animal and drought characteristics.

Asexual reproduction of the new variety by cutting as performed in Visalia and Woodlake, Calif. shows that the foregoing and other distinguishing characteristics come true to form and are established and transmitted through succeeding asexual propagations. 'HIDshurtleff' may be asexually propagated by cutting. The cutting and grafting successfully occurred on the plant/rootstock *Olea* cv. 'MONher' in the United States. Sexual reproduction, such as speed propagation has not been attempted as no seed has formed from this plant.

COMPARISON WITH PARENT/CLOSEST COMMERCIALLY AVAILABLE CULTIVAR

Because the new olive is a naturally occurring mutation, there are no known parents with which to compare the 'HIDshurtleff'. The closest commercially available cultivar to the new variety is the 'MONher' olive (U.S. Plant Pat. No. 5,649). Both olives produce either no fruit or few immature fruits each year. The new olive may be distinguished from the 'MONher' variety by the following combination of characteristics: the 'HIDshurtleff' has a weeping and cascading characteristic and the 'MONher' does not. The 'HIDshurtleff' has fewer lateral branches than does the 'MONher'. In addition, the leaves of the 'HIDshurtleff' are greener and glossy, have a smoother soft texture, and are wider and longer, compared to the foliage of 'Monher'.

BRIEF DESCRIPTION OF ILLUSTRATIONS

The accompanying photographs illustrate a three-year old plant of the new variety and show the leaves and branches thereof depicted in color as nearly correct as it is possible to make in a color illustration of the character. Throughout this specification, color references and/or values are based upon The Colour Chart of The Royal Horticultural Society (2001) except where common terms of color definition are employed, wherein:

Referring to sheet 1:

- the upper left hand photo depicts the whole plant at age 3;
- the upper right hand photo depicts a close-up view of an average trunk of the plant at age 3; and
- the middle and lower photos depict a close-up view of average branches of the plant at age 3.

Referring to sheet 2:

- the upper left photo depicts average leaves of the plant at age 3;
- the upper right photo depicts a close-up of exemplary mature fruit of the plant at age 3;
- the middle left photo depicts a close-up of mature leaves of the plant at age 3;
- the middle right photo depicts the exemplary fruit on a branch of the plant at age 3; and the lower photo depicts the a close-up of the fruit on a branch of the plant at age 3.

DESCRIPTION OF THE NEW VARIETY

The following description is of 4 year-old olive trees of the new variety grown outdoors in Visalia and Woodlake, Calif. from September 2006 to September 2010. Phenotypic expression may vary with environmental, cultural and climatic conditions, as well as differences in conditions of light and soil.

PLANT CHARACTERISTICS

It should be understood that the below measurements are all variable, depending on growing conditions in a season.

Plant form: Weeping.

Growth characteristics:

*Habit*.—Branched and weeping or cascading.

*Age to maturity*.—Three years.

*Mature plant dimensions*.—Height: 1.3 to 4.6 meters with shaping, up to a maximum height of 9 to 10 meters naturally. Diameter: 1 to 3 meters with shaping, up to 4 to 6.2 meters naturally.

*Rootstock*.—*Olea* 'MONher'.

Growth rate/vigor: 0.6 to 0.8 meters per year.

Root:

*Root initiation*.—6 to 8 weeks to initiate roots.

*Root description*.—At maturity spreading and woody.

Foliage:

*Arrangement*.—Opposite.

*Compound or single leaves*.—Single.

*Number*.—Leaflets on normal mid-stem leaves is: 1 (only single leafing habit).

*Quantity*.—Number of leaves per lateral branch is: 10 to 200.

*Color*.—New foliage: Upper side: (green) RHS 137C, Under side: (grayed-green) RHS 192B. Old foliage: Upper side: (green) RHS 137A. Lower side: (grayed-green) RHS 190B.

*Size*.—About 5 to 9 cm long×1.5 to 3 cm wide.

*Shape*.—Inversely lance-shaped (oblanceolate).

*Base shape*.—Auriculate or Cordate.

*Apex shape*.—Acuminate.

*Texture*.—Glossy/smooth.

*Margin*.—Entire.

*Pubescence*.—None.

*Venation pattern*.—Pinnate paired with reticulate.

*Vein color*.—Upper side: (yellow-green) RHS 145B. Under side: (yellow-green) RHS 145B.

*Petiole*.—Color: (green) RHS 145C. Length: 0.5 cm average. Surface Texture: smooth, no stipules, tendrils, thorns, spines or prickles present.

Wood characteristics:

*New wood*.—Color: (grayed-green) RHS 198C. Bark: smooth.

*Old wood*.—Color: (grayed-green) RHS 197C. Bark: smooth.

*Trunk*.—Length: ~5 cm to first branching. Diameter: 3.5 cm at soil level.

*Branching habit*.—Young: Irregular; with an up or lateral habit. Mature: Irregular; with a downward weeping/cascading manner. Lateral Branches: Length: variable ~15 to 60 cm. Diameter: variable ~0.5 to 1 cm. Internode Distance: 1.5 to 1.7 cm. Stem Pubescence Present: No.

Prickles: None.

Flowering characteristic: None

Fruiting characteristic:

*Seed development*.—None, or where present immature and slow with low flesh content.

*Seed length*.—Where present 1 to 1.8 cm or smaller.

*Seed diameter*.—Where present 0.5 to 1.4 cm or smaller.

*Seed color*.—New: (yellow-green) RHS 144A. Old: (black) RHS 202A.

Hardiness:

*Disease resistance*.—Not tested.

*Pest resistance*.—Not tested.

*Winter hardiness*.—U.S. Hardiness zones 6a to 11.

*Drought resistance*.—Yes.

Growing conditions: Outdoor, no special conditions.

What is claimed is:

1. A new and distinct variety of ornamental olive tree, substantially as herein shown and described.

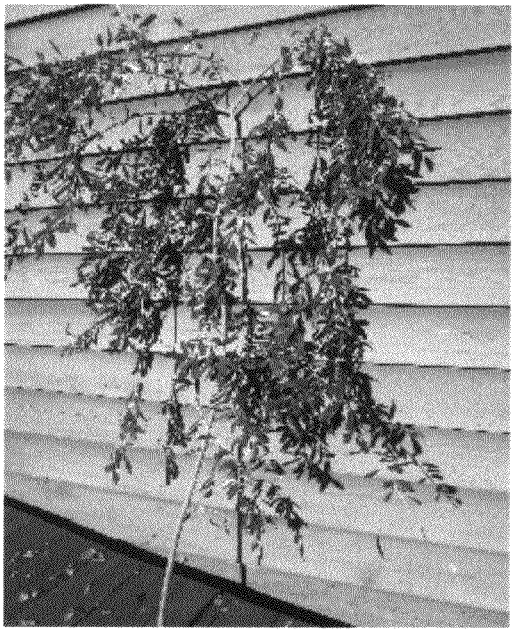
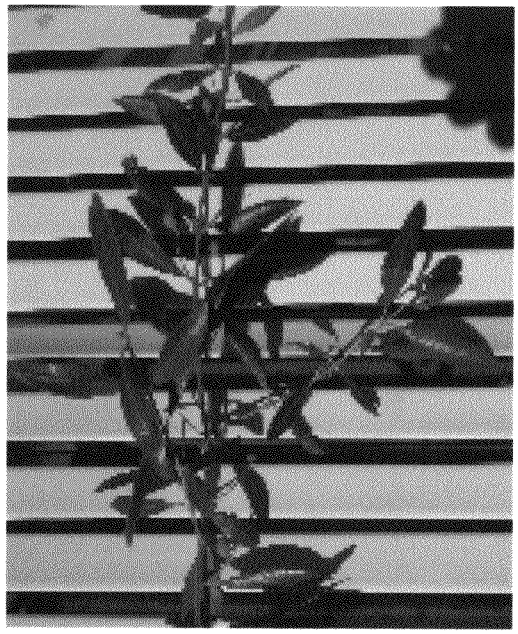
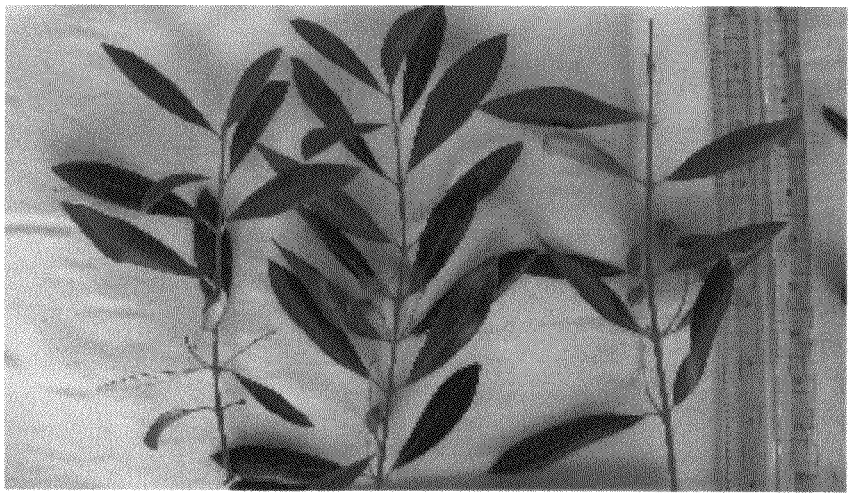
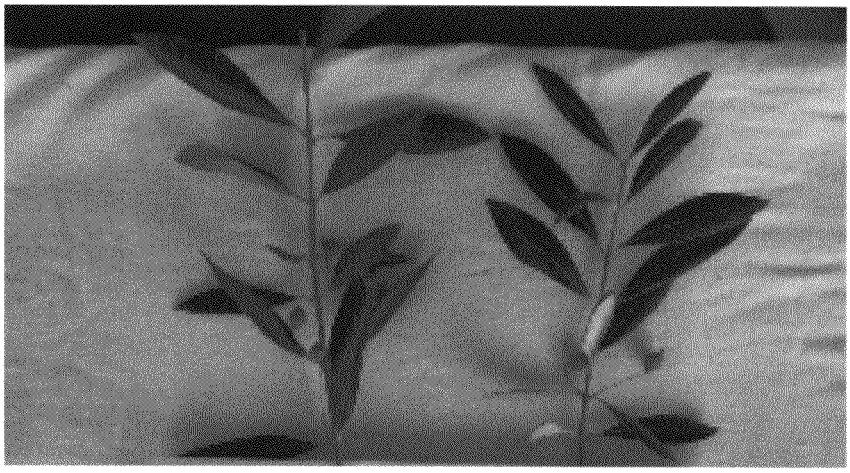

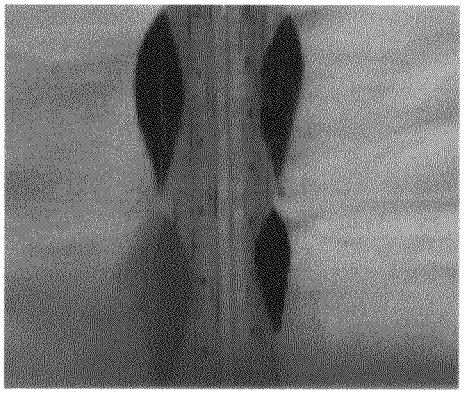
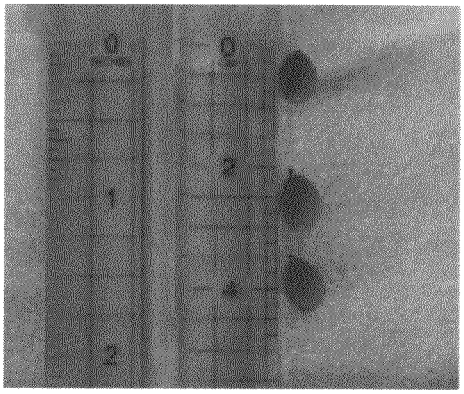
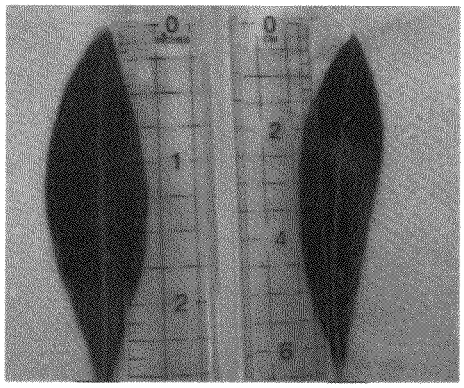
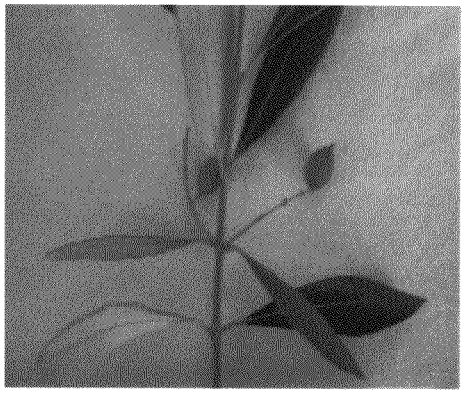
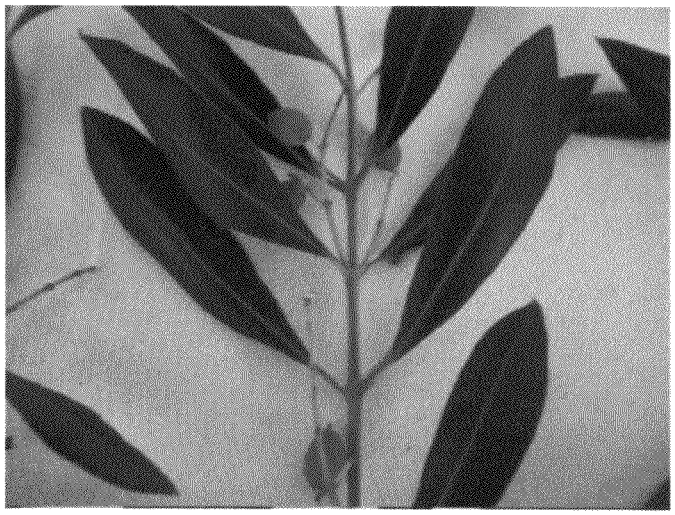

* * * * *